United States Patent [19]

Axelrod

[11] Patent Number: 4,562,011

[45] Date of Patent: Dec. 31, 1985

[54] PROCESS FOR PREPARING ARYL PHOSPHATES

[75] Inventor: Robert J. Axelrod, Glenmont, N.Y.

[73] Assignee: General Electric Company, Pittsfield, Mass.

[21] Appl. No.: 555,720

[22] Filed: Nov. 28, 1983

[51] Int. Cl.$^4$ ............................................. C07F 9/09
[52] U.S. Cl. ............................................. 260/978
[58] Field of Search ............................. 260/966, 978

[56] References Cited

U.S. PATENT DOCUMENTS 1,869,312  7/1932  Granger .............................. 260/978
2,886,586  5/1959  Rinse .................................. 260/980

FOREIGN PATENT DOCUMENTS 763311  12/1956  United Kingdom .

OTHER PUBLICATIONS

Kirk–Othmer, "Encylcopedia of Chemical Technology", vol. 4, (1964), p. 390.

Primary Examiner—Anton H. Sutto
Attorney, Agent, or Firm—Hedman, Gibson, Costigan & Hoare

[57] ABSTRACT

Aryl phosphates are prepared by a procedure in which a diaryl cabonate is reacted with phosphoric acid or a phosphate derived from the acid, using an added source of hydrogen ions, for instance, methanesulfonic acid, to catalyze the reaction.

15 Claims, No Drawings

PROCESS FOR PREPARING ARYL PHOSPHATES

BACKGROUND OF THE INVENTION

Aromatic phosphates are known to be useful as flame retardant agents and plasticizers for thermoplastic polymers and blends, such as compositions of polyphenylene oxide and polystyrene. Various methods for preparing aromatic phosphates (also referred to herein as aryl phosphates) have been described or proposed. For instance, triarylphosphites can be produced by the reaction of phosphorus trihalides, for example, $PCl_3$, with hydroxy-substituted aromatic compounds in the presence of a catalyst (Maul, et al., U.S. Pat. No. 4,312,818) and it is known that, analogously, triarylphosphates can be prepared from the reaction of phosphoryl halides, e.g., $POCl_3$, with hydroxy-substituted aromatic compounds. Other procedures involve the reaction of a phenolic compound with a pentavalent phosphorus compound, e.g., $P_2O_5$, or phosphoric acid, as disclosed in British Pat. No. 763,311, and of a phenolate with a pentavalent phosphorus compound as disclosed in U.S. Pat. No. 2,886,586.

INTRODUCTION TO THE INVENTION

There has now been discovered a new procedure for producing aryl phosphates, which involves reacting a diaryl carbonate with phosphoric acid or a phosphate derivative of the acid, or a mixture of the acid and phosphate, in the presence of hydrogen ions. Optionally, a phenolic compound can also be included in the starting mixture as an additional co-reactant. The aromatic rings in the starting materials can be unsubstituted or substituted with, e.g., alkyl, depending on the final product(s) desired, and the process can be regulated to obtain triaryl phosphate alone or in admixture with other aryl phosphates.

The present process offers the advantage that an acid, for example, hydrochloric, is not produced as a by-product. Moreover, phosphoric acid, which is one of the starting materials, is less corrosive and more easily handled than the stronger acids produced in other processes.

DETAILED DESCRIPTION OF THE INVENTION

The preferred co-reactants in the process are represented by the following formulas:

The Diaryl Carbonate

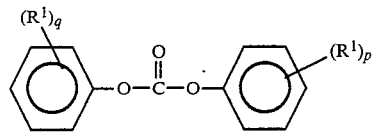

The Phosphoric Acid or Phosphate

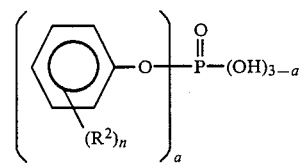

The Phenolic Compound (Optional)

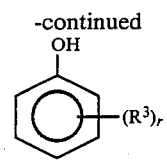

Depending on the reactants, the reaction will result in one or more compounds of the following general formula:

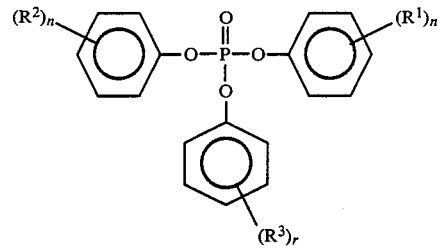

in which in the above formulas $a = 0, 1$ or 2; n, p, q and r are, independently, zero or integers from 1 to the maximum number of replaceable hydrogen atoms on the ring, and $R^1$, $R^2$ and $R^3$ are, independently, alkyl of from 1 to 4 carbon atoms, for example, methyl, ethyl, propyl or butyl.

By way of illustration, in one way of carrying out the process, the reactants and the hydrogen ion source, which is preferably an acid such as methane sulfonic, are placed in a steel or glass-lined reaction vessel that has been equipped with heating means and stirring means. If desired, an additional solvent, such as an inert organic liquid, may be included, although this is not necessary because the acids and phenolics, if present, will function as solvents.

The reactants may be provided in stoichiometrically equivalent amounts, but the reaction will still proceed if an excess of one or the other is used.

Only very small amounts of a source for the hydrogen ions are necessary to effect or facilitate the reaction. The source, e.g., acid, is preferably included in amounts sufficient to provide a concentration of hydrogen ions in the reaction mixture of from about 0.5 to about 1.5% by weight.

To initiate the reaction, the mixture is raised to a sufficient temperature, usually 200° C. or higher. Care should be taken to avoid temperatures above the decomposition points of the reactants and products, and in the usual case the temperature is not allowed to exceed 325° C. The preferred range is between about 210° and about 300° C.

The reactor vessel may also be equipped with a distillation column, by means of which any volatilized solvent and unreacted starting materials are condensed and returned to the reaction mixture and volatile by-products, e.g., phenolics, are removed. Distillation of the byproducts will normally further facilitate the reaction.

The process is preferably carried out at normal (atmospheric) pressure, but superatmospheric pressures may be employed if desired.

The reaction time will vary depending on the amounts of reactants and catalyst (hydrogen ions), the temperature, pressure, and other conditions. Generally, a period of from 2 to 25 hours will be sufficient to complete the reaction and achieve good yields of the end product.

After the reaction has been completed, the mixture may be cooled and the aryl phosphates which have been produced may be separated by use of conventional techniques, such as crystallization or distillation. As an alternative, the aryl phosphate end product or mixture of such phosphates may be separated from the reaction mixture as they are formed during the reaction. This may be accomplished by distilling the reaction mixture under a vacuum equivalent to 0.1 to 10 millimeters of mercury.

The recovered product may be used as is if a liquid, or flaked or granulated if a solid.

DESCRIPTION OF THE SPECIFIC EMBODIMENTS

The invention is illustrated in the following examples, which are presented for instructional purposes only and are not intended as a limitation on the scope.

EXAMPLE 1

The following were placed in a reaction vessel fitted with a distillation column: 4.4 grams of phosphoric acid, 35.8 grams of diphenyl carbonate, 1.1 grams of monophenyl acid phosphate, and 0.3 gram of methane-sulfonic acid. The ingredients were mixed and heated to a temperature of 256° C. for a period of 12 hours. During this period, any phenol which was produced was distilled off. Carbon dioxide gas was also produced, indicating that a reaction was taking place. After 12 hours, the mixture was cooled and a sample was removed. Analysis by gas chromatography confirmed the presence of triphenyl phosphate. The yield was 70% of the theoretical.

EXAMPLE 2

Using the same apparatus as in EXAMPLE 1, a mixture of 59 grams of phosphoric acid, 405 grams of diphenyl carbonate, 129 grams of mesitol and 6 grams of methanesulfonic acid was heated, with continuous stirring, at 275° C. for 21 hours. During this period, by-product phenol was distilled off, and the evolution of carbon dioxide gas bubbles in the reaction mixture was again observed. The phenyl phosphates which were produced were removed as formed by vacuum distillation, using a reduced pressure equivalent to 0.03 millimeters of mercury. The phosphates distilled at pot temperatures of 215° to 240° C. and overhead temperatures of 165° to 190° C. The distillates were cooled and analyzed by gas chromatography, which indicated the presence of triphenyl phosphate, diphenyl mesityl phosphate and dimesityl phenyl phosphate. The total yield was 50% of the theoretical.

All of the above mentioned patents are incorporated herein by reference.

Other variations and modifications of the invention will occur to those skilled in the art in the light of the above disclosure. For instance, the aromatic rings of the starting materials can be substituted in various other positions to yield a different phenyl phosphate or mixture of phosphates. Thus, for example, if trimethyl phenol is replaced with m-cresol (3-methylphenol) in EXAMPLE 2, the final product will be a mixture of triphenyl phosphate, diphenyl cresyl phosphate and dicresyl phenyl phosphate. It is to be understood, therefore, that changes may be made in the embodiments shown which are still within the scope of the invention defined in the appended claims.

We claim:

1. A process for preparing aryl phosphates, comprising reacting a diaryl carbonate with a compound selected from the group consisting of phosphoric acid, aryl phosphate and mixtures of both, in the presence of a source of hydrogen ions.

2. A process according to claim 1, in which the diaryl carbonate has the formula

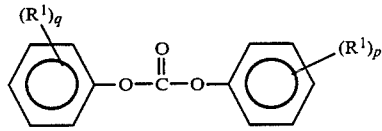

in which $R^1$ is independently allyl of from 1 to 4 carbon atoms, and q and p are, independently, zero or integers from 1 to the maximum number of replaceable hydrogen atoms.

3. A process according to claim 1, in which the phosphoric acid or acid phosphate has the formula

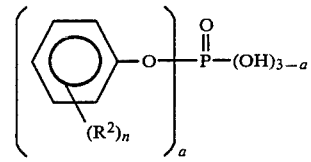

in which $R^2$ is, independently, allyl of from 1 to 4 carbon atoms, n is zero or an integers from 1 to the maximum number of replaceable hydrogen atoms, and a is zero, 1 or 2.

4. A process according to claim 1, in which comprises further including a phenolic compound in the reaction mixture.

5. A process according to claim 4, in which the phenolic compound has the formula

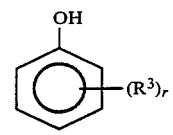

in which R is, independently, allyl of from 1 to 4 carbon atoms, and r is zero or an integer from 1 to the maximum number of replaceable hydrogen atoms.

6. A process according to claim 1, in which the reaction is conducted at a temperature of at least 200° C.

7. A process according to claim 1, in which the reaction temperature is in the range from about 210° to about 300° C.

8. A process according to claim 1, in which the concentration of hydrogen ions in the reaction mixture is from about 0.5 to about 1.5 percent by weight, based on the total weight of the mixture.

9. A process according to claim 1, in which the source of hydrogen ions is an acid.

10. A process according to claim 6, in which the acid is methane sulfonic.

11. A process according to claim 1, in which the end product is triphenyl phosphate, alone or in admixture with one or more other phenyl phosphates.

12. A process according to claim 8, in which the end product is triphenyl phosphate.

13. A process according to claim 9, in which the starting reactants are diphenyl carbonate, phosphoric acid and monophenyl acid phosphate.

14. A process according to claim 11, in which the end product is a mixture of triphenyl phosphate, diphenyl mesityl phosphate and dimesityl phenyl phosphate.

15. A process according to claim 14, in which the starting reactants are diphenyl carbonate, phosphoric acid and trimethyl phenol.

* * * * *